US010890632B2

(12) United States Patent
Habara et al.

(10) Patent No.: US 10,890,632 B2
(45) Date of Patent: Jan. 12, 2021

(54) MAGNETIC RESONANCE IMAGING APPARATUS, Q-VALUE CALCULATION METHOD, AND SPECIFIC ABSORPTION RATE MANAGEMENT METHOD

(71) Applicant: Hitachi, Ltd., Tokyo (JP)

(72) Inventors: Hideta Habara, Tokyo (JP); Masaharu Ono, Tokyo (JP); Tetsuhiko Takahashi, Tokyo (JP); Hiroyuki Takeuchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 344 days.

(21) Appl. No.: 16/083,969

(22) PCT Filed: Feb. 14, 2017

(86) PCT No.: PCT/JP2017/005201
§ 371 (c)(1),
(2) Date: Sep. 11, 2018

(87) PCT Pub. No.: WO2017/159168
PCT Pub. Date: Sep. 21, 2017

(65) Prior Publication Data
US 2020/0309874 A1    Oct. 1, 2020

(30) Foreign Application Priority Data
Mar. 15, 2016  (JP) .................... 2016-051327

(51) Int. Cl.
*G01R 33/28* (2006.01)
*A61B 5/055* (2006.01)
(Continued)

(52) U.S. Cl.
CPC ............ *G01R 33/288* (2013.01); *A61B 5/055* (2013.01); *G01R 33/3607* (2013.01);
(Continued)

(58) Field of Classification Search
CPC .............. G01R 33/288; G01R 33/3607; G01R 33/4802; G01R 33/5608; G01R 33/5612; A61B 5/055
See application file for complete search history.

(56) References Cited

U.S. PATENT DOCUMENTS 8,102,177 B2    1/2012 McKinnon
2011/0043205 A1*  2/2011 Graesslin .......... G01R 33/5612
                                                        324/307
(Continued)

FOREIGN PATENT DOCUMENTS

JP           5337162 B2     11/2013
WO        2016009791 A1      1/2016

OTHER PUBLICATIONS

Mansfield, P. et al., "NMR imaging in biomedicine", Academic Press. NY. 1982, p. 313.
(Continued)

*Primary Examiner* — Gregory H Curran
(74) *Attorney, Agent, or Firm* — Baker Botts L.L.P.

(57) ABSTRACT

To avoid the complication of an MRI apparatus and avoid the overestimation of a calculated value of SAR without extending a processing time and to perform accurate SAR management. To this end, the MRI apparatus is equipped with a high frequency antenna which has a plurality of channels and resonates at a predetermined frequency, and a measuring instrument which measures the amplitudes of a forward traveling and reflected waves of each high frequency signal supplied to the high frequency antenna. In the MRI apparatus, a reflection matrix S is determined based on the measured amplitudes. Diagonal terms of the determined reflection matrix S are used to calculate Q values for each of the channels. Each non-diagonal term of the reflection matrix S is used to correct the calculated Q value. The corrected Q value is used to calculate irradiation power (Continued)

consumed in a subject among irradiation power from the high frequency signals supplied to the high frequency antenna when imaging to thereby manage a specific absorption rate.

6 Claims, 5 Drawing Sheets

(51) Int. Cl.
    *G01R 33/36*     (2006.01)
    *G01R 33/48*     (2006.01)
    *G01R 33/56*     (2006.01)
    *G01R 33/561*    (2006.01)

(52) U.S. Cl.
    CPC ..... *G01R 33/4802* (2013.01); *G01R 33/5608* (2013.01); *G01R 33/5612* (2013.01)

(56) References Cited

U.S. PATENT DOCUMENTS

| | | |
|---|---|---|
| 2011/0181287 A1 | 7/2011 | Ito et al. |
| 2014/0232401 A1* | 8/2014 | Takagi ................. G01R 33/543 |
| | | 324/309 |
| 2015/0002147 A1 | 1/2015 | Fontius et al. |
| 2016/0128574 A1* | 5/2016 | Rutt ................... G01R 33/5612 |
| | | 600/410 |
| 2017/0146620 A1 | 5/2017 | Habara et al. |

OTHER PUBLICATIONS

Adam Abramowicz, "Transformer model based on admittance inverter", The 8th international Conference on Electrical and control technologies, 2013, Proceedings p. 154.

International Search Report for PCT Application No. PCT/JP2017/005201, dated Apr. 25, 2017, 4 pages.

* cited by examiner

MAGNETIC RESONANCE IMAGING APPARATUS, Q-VALUE CALCULATION METHOD, AND SPECIFIC ABSORPTION RATE MANAGEMENT METHOD

CROSS-REFERENCE TO RELATED APPLICATIONS

This application is a national phase claiming the benefit of and priority to International Patent Application No. PCT/JP2017/005201, entitled "MAGNETIC RESONANCE IMAGING APPARATUS, Q-VALUE CALCULATION METHOD, AND SPECIFIC ABSORPTION RATE MANAGEMENT METHOD", filed Feb. 14, 2017, which claims priority to Japanese Patent Application No. 2016-051327, filed Mar. 15, 2016, which are hereby incorporated by reference in their entireties.

TECHNICAL FIELD

The present invention relates to a magnetic resonance imaging apparatus, and particularly to a technique which controls a specific absorption rate SAR (Specific Absorption Rate) as an index indicating the influence of a high frequency signal to a human body.

BACKGROUND ART

A magnetic resonance imaging (Magnetic Resonance Imaging) apparatus (hereinafter called "MRI apparatus") irradiates a subject disposed in a uniform static magnetic field generated by a static magnetic field magnet with a high frequency signal (hereinafter referred to as "RF signal") being an electromagnetic wave to excite nuclear spins in the subject and receives an NMR signal being an electromagnetic wave generated by the nuclear spins to perform its signal processing, thereby obtaining a magnetic resonance image of the subject.

Thus, since the subject is irradiated with the high frequency signal, it is necessary for the MRI apparatus to perform control to prevent a temperature rise or burns from occurring in the subject by heating action of the RF signal. Therefore, a safety standard such as IEC (International Electrotechnical Commission) or the like is provided for a SAR being a specific absorption rate in the human body of the RF signal (radio wave). The MRI apparatus manages the SAR strictly and accurately in accordance with this standard (specific absorption rate management or SAR management). Usually, the MRI apparatus which produces a static magnetic field of 3 Tesla or more monitors the irradiation power of the RF signal in real time by means of a SAR monitor and performs SAR management.

Here, the irradiation of the RF signal and the reception of the NMR signal are carried out by an antenna device (hereinafter referred to as "RF antenna") called an RF antenna or an RF coil which transmits or receives electromagnetic waves of a radio frequency. Irradiation power $P_{input}$ of each RF signal input to the RF antenna is represented by the sum of antenna consumed power $P_{antenna}$ which is consumed by the RF antenna and causes heat generation of the RF antenna, and subject consumed power $P_{object}$ which is consumed by the subject and causes heat generation of the subject, like the following formula (1).

[Formula 1]

$$P_{input} = P_{antenna} + P_{object} \quad (1)$$

It is necessary to grasp the exact subject consumed power $P_{object}$ for the execution of accurate SAR management. The subject consumed power $P_{object}$ can be calculated using, for example, a Q value of resonance of the RF antenna. That is, a Q value $Q_{empty}$ in a state in which no subject (patient) is placed inside the RF antenna, and a Q value $Q_{loaded}$ in a state in which the subject is placed thereinside are acquired by measurement. The subject consumed power $P_{object}$ can be calculated by the following formula (2) using these values (for example, Non-Patent Literature 1):

[Formula 2]

$$P_{object} = P_{input} * \left(1 - \frac{Q_{loaded}}{Q_{empty}}\right) \quad (2)$$

CITATION LIST

Patent Literature

PTL 1: U.S. Pat. No. 8,102,177B2 Specification

Non-Patent Literature

NON-PTL 1: Mansfield, P. et al., "NMR imaging in biomedicine", Academic Press. NY. 1982, p 313

NON-PTL 2: Adam Abramowicz, "Transformer model based on admittance inverter", The 8th international Conference on Electrical and control technologies, 2013, Proceedings p 154.

SUMMARY OF INVENTION

Technical Problem

Meanwhile, the recent MRI apparatus tends to increase a transmission channel (hereinafter simply referred to as "channel") of an RF antenna in plural form (e.g., 2 to 16 channels). There has also been made such a contrivance that a plurality of channels are provided to achieve spatial uniformization of irradiation with different irradiation power and phases in the respective channels. When the RF antenna provided with the plural channels is used, there is a need to measure Q values and perform the calculation of the above-described formulas (1) and (2) for all channels for the purpose of obtaining accurate subject consumed power $P_{object}$.

However, when, in an RF antenna having two or more channels, there is a coupling between the channels, it is difficult to accurately obtain the Q value in the formula (2). Generally, when there is a coupling between channels, the Q value of each antenna is reduced as compared with a case where there is no coupling. Further, since the coupling between the channels becomes large where a subject is placed, a loaded $Q_{loaded}$ rather than an unloaded $Q_{empty}$ is susceptible to the coupling, and the Q value is more reduced.

When the $Q_{loaded}$ is measured less under the influence of the coupling between the channels, the subject consumed power $P_{object}$ is estimated to be higher than actual (refer to the formula (2)). This is due to the fact that actually despite the $Q_{loaded}$ is originally a higher value, it is measured less.

When the subject consumed power $P_{object}$ is estimated to be higher than actual, though the RF signal applied to the human body is irradiation power less than its upper limit value determined in the safety regulations, the MRI apparatus assumes the RF signal to have been irradiated to the upper limit value. Therefore, a restriction on RF signal irradiation is taken in a value lower than original. The MRI apparatus will cause failures such as prolongation of the time required to acquire an image, a decrease in the number of images to be acquired, degradation in an image due to the acquisition of the image without sufficiently irradiating each RF signal, etc.

Incidentally, the Q value can also be determined by measuring the reflection coefficient (S parameter) S of each channel of the antenna and performing impedance conversion of the reflection coefficient S. Specifically, the Q value can be calculated by dividing a resonant frequency by a frequency difference between two points indicating a value smaller $1/\sqrt{2}$ than a maximum peak (impedance peak) value of the resonance in an LC circuit. When impedance-converting the reflection coefficient S, phase information (angle, complex number, etc.) of the reflection coefficient S is required.

However, in general, the phase information of the reflection coefficient S is required to detect a phase relationship between a transmission wave and a reflected wave. An expensive device such as a network analyzer is required for the detection.

Since the MRI apparatus which generates the static magnetic field of 3 tesla or more is normally provided with a measuring instrument which measures the forward traveling wave and the reflected wave of the RF signal in real time, it is possible to relatively easily measure the absolute value of the reflection coefficient S by use of the measuring instrument. However, since a detector for the RF signal having the forward traveling and reflected waves is required for the measurement of the phase information of the reflection coefficient S, the apparatus is made complex. There is considered a case where the phase information of the reflection coefficient S is measured using a reception system of the MRI apparatus instead of the detector. In this case, however, a path different from a path to receive a normal MRI signal is made necessary, and equipment such as an RF attenuator, an RF switch or the like corresponding to high power is required. After all, the apparatus is made complex.

There has been proposed in Patent Literature 1, a method of upon SAR management, calculating an irradiation antenna and a load of a subject placed thereinside as admittances $Y_{coil}$ and $Y_{object}$ respectively, and multiplying them by an input voltage $V_{in}$ to thereby calculate $P_{object}$ and $P_{coil}$. It was found that when applying this method to a four-channel system of irradiation coil as an example, the excessive estimation of $P_{object}$ was somewhat solved, but all overestimation was not eliminated. Further, in the method of Patent Literature 1, the phase information of the reflection coefficient S is also required to be measured upon the calculation of the admittance Y, and after all the apparatus is made complicated.

It has also recently been made possible to measure the Q value by using the information of the absolute value of the reflection coefficient S without measuring the phase information (angle, complex number, etc.) of the reflection coefficient S. However, when there is a coupling between the channels in the RF antenna, it is difficult to calculate an accurate Q value.

Here, the magnitude of the coupling between the channels in the RF antenna refers to, for example, a magnitude at which in the case of two channels, RF transmitted from the channel 1 leaks out from the channel 2. When the coupling between the channels is large, the amount of RF entered from the channel 1, which comes out from the channel 2 is also increased. No existence of the coupling or a state in which the coupling is hardly present is ideal. A reference to the state in which the coupling is hardly present is that the power which enters from the channel 1 and comes out from the channel 2 is 0.01% or less (−40 dB) below as a measure.

When there is a coupling, it is difficult to theoretically elucidate by the Q value for each channel and the reflection coefficient S of the RF antenna, the relationship between the power incident to the RF antenna and the power consumed by the subject, which varies depending on the RF antenna having plural channels and the positional relationship of the subject to the RF antenna.

On the other hand, the electromagnetic field numerical simulation has been developed in recent years, and a relatively accurate calculation has become possible even in a coupling-existing system. That is, when human bodies different in size are arranged in various imaging positions inside the MRI apparatus, the relationship of Q, S, $P_{antenna}$, and $P_{object}$ can be known by executing the electromagnetic field numerical simulation.

The electromagnetic field numerical simulation is thus useful for obtaining $P_{object}$ accurate to some degree. Since, however, a long calculation time is required, the actual MRI apparatus is currently not capable of performing simulation calculations simultaneously with the imaging and managing the SAR in time for the imaging. More specifically, it takes at least several dozens of minutes and a few hours at the longest to perform the electromagnetic field numerical simulation. The electromagnetic field numerical simulation is performed during imaging in which one imaging time per person is about 20 minutes. Thus, it is not practical to apply an SAR estimated value calculated from this result to the SAR management.

Thus, when the coupling exists between the channels in the RF antenna having the plural channels, it is difficult to accurately calculate the Q value, let alone to calculate the SAR estimated value. It is not sufficient to carry out the SAR management accurately and promptly.

The present invention has been made in view of the above circumstances and aims to avoid overestimation of a SAR calculation value without complicating an apparatus and extending a processing time, and further to perform SAR management accurately.

Solution to Problem

One aspect of the present invention provides a magnetic resonance imaging apparatus equipped with a high frequency antenna which has a plurality of channels and resonates at a predetermined frequency, a supply unit which supplies a plurality of high frequency signals having different frequencies to the high frequency antenna, a measuring instrument which measures the amplitudes of a forward traveling wave and a reflected wave of each of the high frequency signals supplied from the supply unit to the high frequency antenna, a Q-value calculation unit which calculates a Q value for each of the channels by fitting an absolute value of each diagonal term of a reflection matrix S calculated based on the amplitudes measured by the measuring instrument to a predetermined circuit model, and a Q-value correction unit which corrects the Q value calculated by the Q-value calculation unit using an absolute value of each non-diagonal term of the reflection matrix S.

Advantageous Effects of Invention

According to the present invention, it is possible to avoid overestimation of an SAR calculation value without complicating an apparatus and extending a processing time and further to perform SAR management accurately.

DESCRIPTION OF EMBODIMENTS

An MRI apparatus according to one embodiment of the present invention will hereinafter be described with reference to the drawings.

[Overall Configuration of MRI Apparatus]

Figure 1:
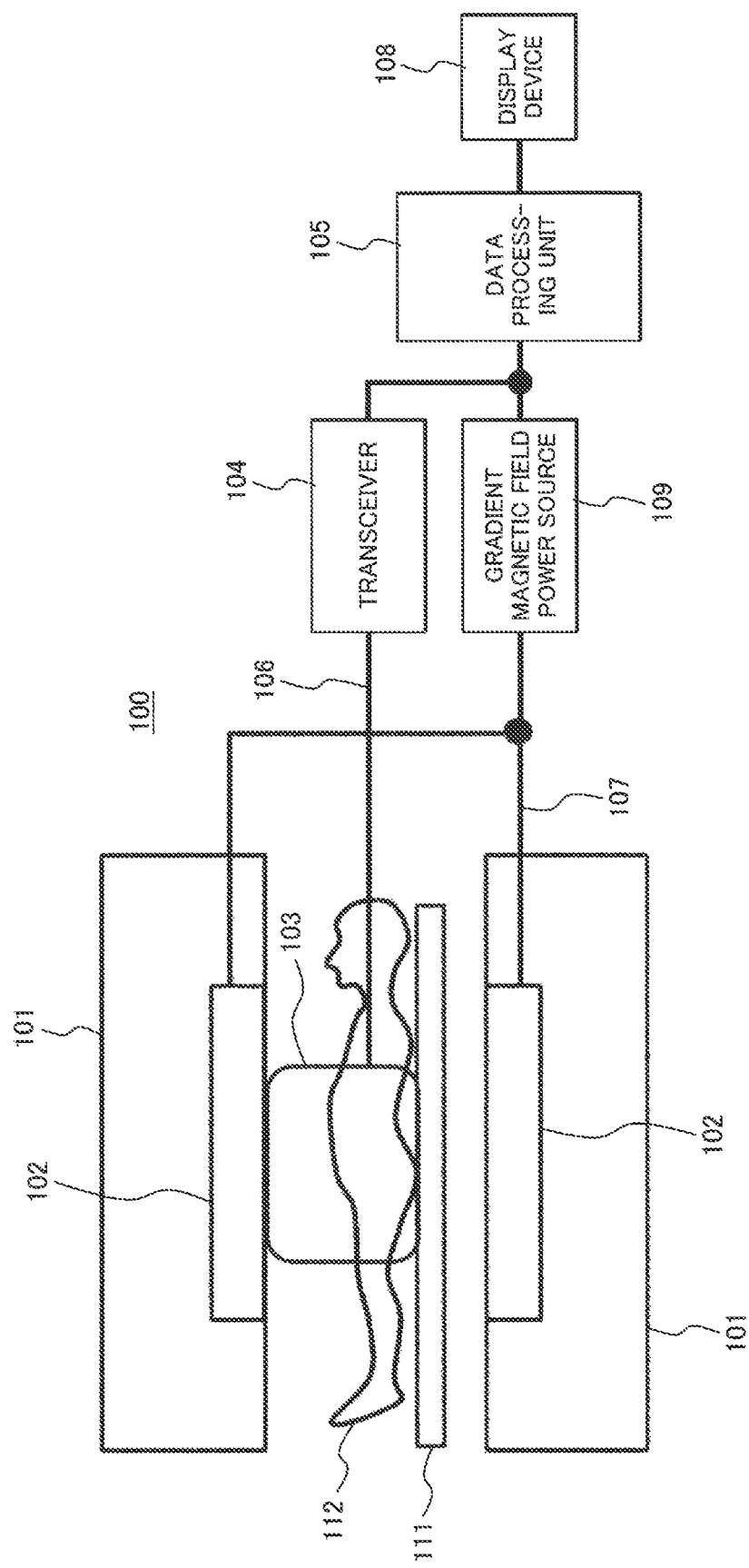
FIG. 1 is a schematic configuration diagram of an MRI apparatus according to an embodiment of the present invention.

As shown in FIG. 1, there is provided a schematic configuration diagram of an MRI apparatus 100 according to the present embodiment. The MRI apparatus 100 is equipped with a magnet 101 which forms a static magnetic field in a measurement space in which a subject 112 is placed, a gradient magnetic field coil 102 which applies a magnetic field gradient in a predetermined direction to the static magnetic field, an RF antenna 103 which transmits each high frequency signal (RF signal) to the subject 112 and receives each nuclear magnetic resonance signal (NMR signal) generated from the subject 112, a transceiver 104 which generates a pulse waveform of the RF signal (RF wave) and transmits the same to the RF antenna 103 and which performs signal processing on the NMR signal received by the RF antenna 103, a gradient magnetic field power source 109 which supplies a current to the gradient magnetic field coil 102, a data processing unit 105 which controls driving of the transceiver 104 and the gradient magnetic field power source 109 and accepts various information processing and operations by an operator, a display device 108 for displaying a result of processing by the data processing unit 105, and a bed 111 which places the subject 112 thereon.

The gradient magnetic field power source 109 and the gradient magnetic field coil 102 are connected by a gradient magnetic field control cable 107. Further, the RF antenna 103 and the transceiver 104 are connected by a transmission/reception cable 106 which transmits and receives signals between the RF antenna 103 and the transceiver 104. The transceiver 104 is equipped with a synthesizer, a power amplifier, a reception mixer, an analog-digital converter, a transmission/reception changeover switch, etc. (all not shown).

The RF antenna 103 resonates at a predetermined frequency and includes a multi-channel transmission having two or more channels, or a transmission/reception antenna.

Incidentally, although the example illustrated in FIG. 1 shows a single RF antenna as the RF antenna 103 which performs transmission of the RF signal and reception of the NMR signal, the present example is not limited to it. For example, an RF antenna comprised of a plurality of antennas may be used as the RF antenna 103 as in the case where a wide-range imaging RF antenna and a local RF antenna are combined, etc. Particularly, when each region of a human body is imaged in detail, an antenna for transmission and an antenna for reception, which are different from each other, are used in most cases. A large irradiation antenna installed inside the gradient magnetic field coil which covers the whole body is often used for transmission, and a local antenna arranged near the surface of the human body is often used for reception. In this case, the local antenna is only for reception in most cases. There is also a case where a local transmission/reception antenna is used which is locally disposed near the human body partly and performs both of transmission and reception. The local transmission/reception antenna in this case is also often configured by a plurality of channels.

The MRI apparatus 100 is divided into a horizontal magnetic field system and a vertical magnetic field system according to the direction of the static magnetic field formed by the magnet 101. In the case of the horizontal magnetic field system, generally, the magnet 101 has a cylindrical bore (center space) and generates a static magnetic field from side to side in FIG. 1, and is called a tunnel type MRI apparatus. On the other hand, in the case of the vertical magnetic field system, a pair of magnets is vertically arranged with the subject 112 interposed therebetween, and generates a vertical static magnetic field in FIG. 1.

The data processing unit 105 controls the transceiver 104 and the gradient magnetic field power source 109 and intermittently applies an RF signal and applies a gradient magnetic field from the RF antenna 103 and the gradient magnetic field coil 102 to the subject 112 placed in the static magnetic field. Further, an NMR signal generated from the subject 112 in resonance with the RF signal is received by the RF antenna 103, where signal processing is performed thereon to reconstruct an image. The subject 112 is, for example, a predetermined region of the human body. Further, the data processing unit 105 calculates a Q value at each channel of the RF antenna 103 and performs SAR management based on the Q value. The details of the calculation of the Q value and the SAR management in the data processing unit 105 will be described below.

[Configuration of RF Transmission/Reception System]

Figure 2:
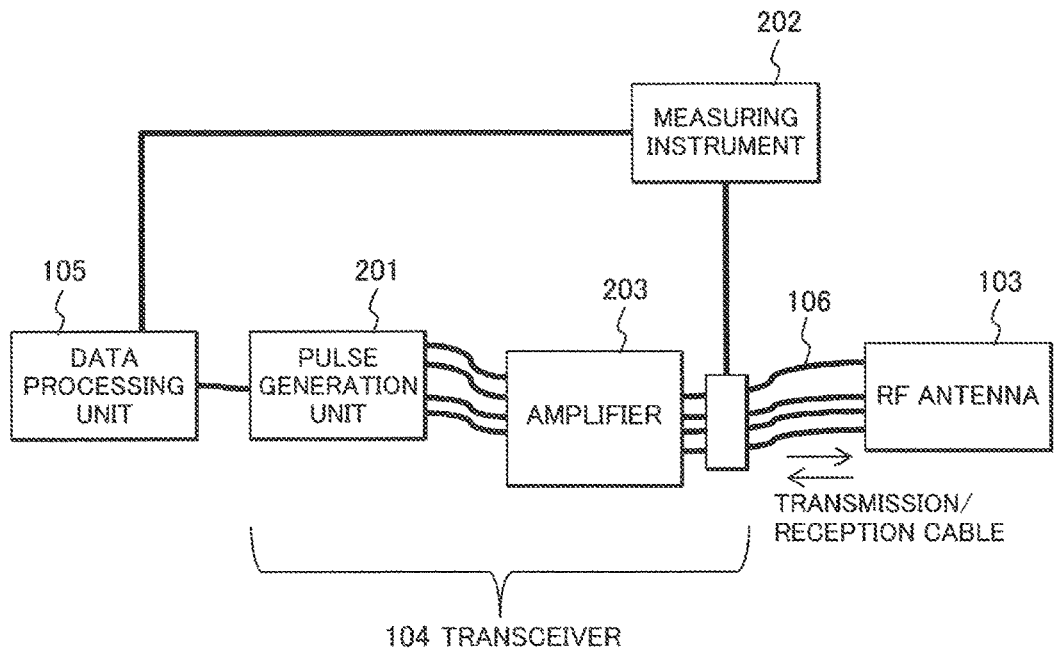
FIG. 2 is a block diagram of an RF transmission system in the embodiment of the present invention.

FIG. 2 shows the details of the configuration of an RF transmission system in the MRI apparatus shown in FIG. 1. As shown in FIG. 2, the RF transmission system includes the transceiver 104, the transmission/reception cable 106, and the RF antenna 103. Here is illustrated a case where the RF antenna 103 includes four channels.

The transceiver 104 is equipped with a pulse generation unit 201, an amplifier 203, and a measuring instrument 202.

The pulse generation unit 201 generates a pulse waveform (transmission RF pulse) of the RF signal transmitted from the RF antenna 103. The transmission RF pulse is normally generated as a signal whose peak power is a few milliwatts or less and input to the amplifier 203. Incidentally, the transmission RF pulse is generated for each channel of the RF antenna 103.

The amplifier 203 amplifies the input transmission RF pulse to an RF wave whose peak power is a few kilowatts and transmits the same to the RF antenna (RF antenna) 103.

The transmission/reception cable 106 is an RF coaxial cable which connects between the pulse generation unit 201 and the RF antenna 103 through the amplifier 203. A high breakdown voltage RF coaxial cable is required to be provided between the amplifier 203 and the RF antenna 103. In the present embodiment, the pulse generation unit 201 and the RF antenna 103 are connected for each channel. Therefore, the transmission/reception cable 106 is provided by the same number as that of channels. Since the RF antenna 103 has the four channels in the example shown in FIG. 2, the RF antenna 103 and the pulse generation unit 201 are connected by four transmission/reception cables 106.

The measuring instrument 202 measures the amplitudes of forward traveling and backward traveling waves of each high frequency signal (RF signal) supplied through the transmission/reception cable 106 to the RF antenna 103 via an RF directional coupler provided between the amplifier 203 and the RF antenna 103. The forward traveling wave is an RF signal directed from the amplifier 203 to the RF antenna 103, and the backward traveling wave is an RF signal which travels in a direction opposite to that of the forward traveling wave. The backward traveling wave is one obtained by superimposing a reflected wave in which the forward traveling wave is reflected by the RF antenna 103 and each of waves sneaking from other plural channels of the RF antenna 103. The backward traveling wave travels from the RF antenna 103 to the amplifier 203.

Generally, when only one arbitrary channel of the plural channels performs transmission, waves reversely sneaked from other channels to the channel which performs transmission are zero. Therefore, in the present embodiment, a reflection coefficient is calculated where the backward traveling waves all become reflected waves of transmission waves, assuming that the number of channels which perform transmission simultaneously is limited to one, and the waves sneaked from other channels are made zero.

The measuring instrument 202 monitors the forward traveling wave and the reflected wave for each channel and outputs their amplitudes to the data processing unit 105. Incidentally, although there is shown in FIG. 2, the example in which the measuring instrument 202 and the amplifier 203 are arranged separately and independently, the measuring instrument 202 may be built in the amplifier 203.

[Configuration of Data Processing Unit]

The data processing unit 105 according to the present embodiment will next be described.

The data processing unit 105 calculates an apparent Q value $Q_{appear}$ for each channel of the RF antenna 103 by using diagonal terms of a reflection matrix indicative of a reflection coefficient S shown in a formula (3). Further, the calculated apparent Q value $Q_{appear}$ is corrected using each non-diagonal term of the reflection matrix indicative of the reflection coefficient S shown in the formula (3) to thereby calculate the original Q value. Then, SAR management at the time of imaging is performed using the calculated Q value.

[Formula 3]

$$S = \begin{pmatrix} S_{11} & \cdots & S_{1j} & \cdots & S_{1M} \\ \vdots & \ddots & \vdots & \ddots & \vdots \\ S_{i1} & \cdots & S_{ij} & \cdots & S_{iM} \\ \vdots & \ddots & \vdots & \ddots & \vdots \\ S_{M1} & \cdots & S_{Mj} & \cdots & S_{MM} \end{pmatrix} \quad (3)$$

Where i and j are channel numbers. Further, the formula (3) indicates S parameters where the number of channels is M.

Here, the apparent Q value $Q_{appear}$ is calculated at a Q-value calculation unit 213 to be described later from the reflection coefficient S determined by a reflection coefficient determination unit 214 by using the amplitudes of forward traveling and reflected waves actually measured by the measuring instrument 202. Thus, since the apparent Q value $Q_{appear}$ is calculated based on the actual measurement values, the apparent Q value $Q_{appear}$ is a value including the influence due to coupling. Accordingly, the influence of the coupling is required to be removed in order to accurately evaluate the Q value. The data processing unit 105 corrects the apparent Q value $Q_{appear}$ to calculate the original Q value. Then, SAR management is carried out based on the so-obtained original Q value.

Figure 3:
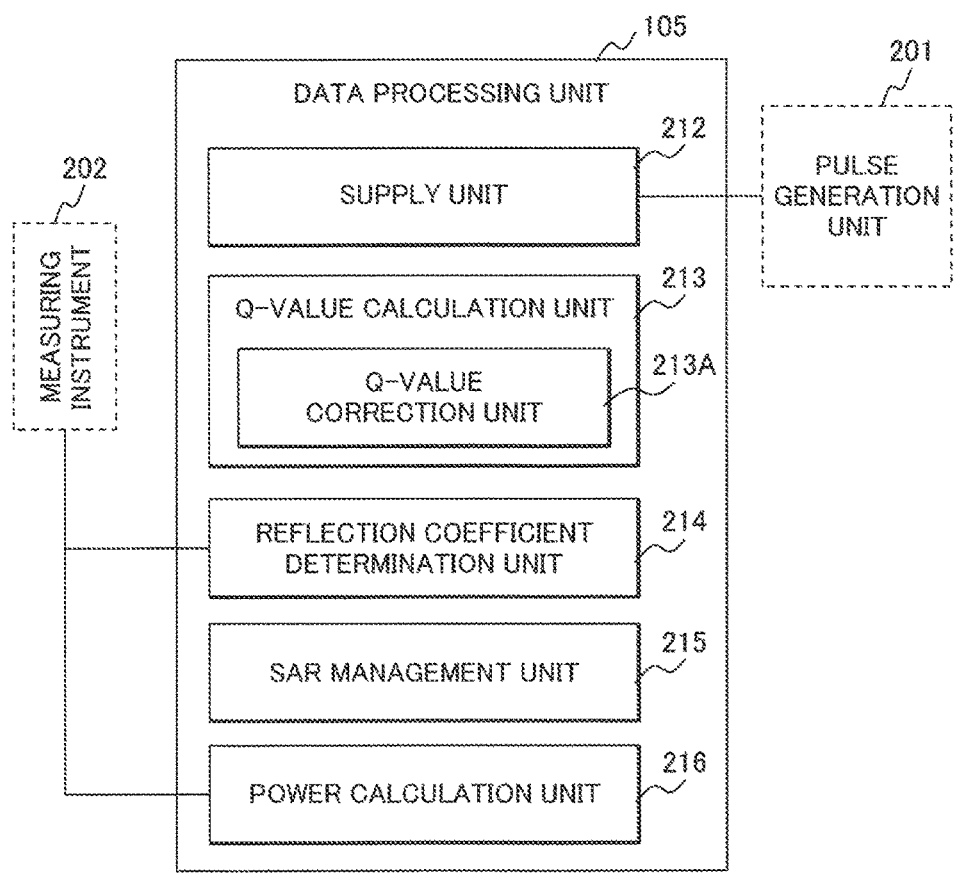
FIG. 3 is a functional block diagram of a data processing unit in the embodiment of the present invention.

The data processing unit 105 is equipped with a supply unit 212, the Q-value calculation unit 213, the reflection coefficient determination unit 214, an SAR management unit 215, and a power calculation unit 216 as shown in FIG. 3 in order to realize the abovementioned processing.

The supply unit 212 supplies a high frequency signal (RF signal) to the RF antenna 103. Specifically, the supply unit 212 instructs the pulse generation unit 201 to generate an RF pulse waveform supplied to each channel of the RF antenna 103.

The reflection coefficient determination unit 214 calculates an absolute value of each diagonal term of the reflection coefficient S and an absolute value of each non-diagonal term thereof for each channel. The absolute values of the diagonal and non-diagonal terms of the reflection coefficient S are respectively obtained by calculating the square root of a value obtained by dividing the amplitude of power of the reflected wave by the amplitude of power of the forward traveling wave. The reflection coefficient determination unit 214 calculates and determines non-diagonal terms $S_{ij}(i \neq j)$ of the reflection coefficient S and diagonal terms $S_{ij}(i=j)$ thereof over a certain frequency range.

The Q-value calculation unit 213 calculates, for each imaging, each subject and each imaging region, a Q value from the absolute value of each diagonal term of the reflection coefficient S determined by the reflection coefficient determination unit 214 by using the amplitudes of the forward traveling wave and the reflected wave measured by the measuring instrument 202 in a state in which the subject 112 is placed inside the RF antenna 103 in the form of the imaging time, i.e., in a load state at the imaging. That is, the Q-value calculation unit 213 calculates $Q_{loaded}$ in the following formula (4).

Further, the Q-value calculation unit 213 calculates a Q value $Q_{empty}$ of the RF antenna 103 using the amplitudes of the forward traveling wave and the reflected wave measured by the measuring instrument 202 and the absolute value of the diagonal term of the reflection coefficient S determined by the reflection coefficient determination unit 214 in a state (no-load state) in which no subject is placed inside the RF antenna 103, i.e., no load is placed.

[Formula 4]

$$P_{object} = P_{input} * \left(1 - \frac{Q_{loaded}}{Q_{empty}}\right) \quad (4)$$

Here, $P_{object}$ is power consumed by the subject, $P_{input}$ is irradiation power of the RF signal input to the RF antenna, and $Q_{empty}$ is the Q value in a state in which no subject (patient) is placed inside the RF antenna.

That is, the Q-value calculation unit 213 calculates a Q value at the time of no load and determines $Q_{empty}$ at timing different from that at the imaging in order to measure the Q value $Q_{empty}$ at the no load and store the same as data. As the timing different from that at the imaging, there are considered, for example, those at the time of the manufacture of the MRI apparatus 100, the time of its setting-up (its installation), the time of its adjustment, the time of its maintenance, etc. More specifically, there is considered when replacing the parts relating to a transmission system, the amplifier 203, the RF antenna 103, the transmission/reception changeover switch, the transmission/reception cable 106, etc. when the MRI apparatus 100 is installed in a hospital or the like. The MRI apparatus performs determining processing of the reflection coefficient in such a no-load state in which the subject is not placed. The Q-value calculation unit 213 calculates a Q value $Q_{empty}$ of the RF antenna 103, based on the result of its processing.

The Q value $Q_{loaded}$ and the Q value $Q_{empty}$ calculated at the Q-value calculation unit 213 are Q values calculated from only the diagonal terms of the reflection coefficient S of the RF antenna with coupling, and are values including the influence of the coupling. Therefore, both are the above-described apparent Q value $Q_{appear}$. To this end, the Q-value calculation unit 213 is equipped with a Q-value correction unit 213A to correct the apparent Q value $Q_{appear}$.

The Q-value correction unit 213A estimates the ratios of energy consumed by the RF antenna 103, of energy of the RF signal input to the RF antenna 103, and energy thereof consumed in the subject being an irradiated object of the RF signal, which is arranged near the RF antenna 103 to thereby correct the Q value. Specifically, the Q-value correction unit 213A corrects the apparent Q value $Q_{appear}$ using the absolute value of each non-diagonal term of the reflection coefficient S to thereby calculate the original Q value $Q_0$.

The power calculation unit 216 calculates the irradiation power $P_{input}$ by the RF signal supplied to the RF antenna 103 at the imaging by referring to the value of the measuring instrument 202.

The SAR management unit 215 calculates irradiation power affecting the subject 112, of the irradiation power $P_{input}$ calculated by the power calculation unit 216, i.e., subject consumed power $P_{object}$ in accordance with the above formula (4) by using the Q value calculated by the Q-value calculation unit 213 and corrected by the Q-value correction unit 213A and calculates a specific absorption rate SAR.

That is, in the present embodiment, the Q value $Q_{loaded}$ during imaging of the subject, which is calculated by the Q-value calculation unit 213 and corrected by the Q-value correction unit 213A, and the Q value $Q_{empty}$ at no load when installing or the like are used to calculate the subject consumed power $P_{object}$ in accordance with the above formula (4) and then calculate the SAR, whereby SAR management is performed.

Subsequently, the SAR management by the SAR management unit 215 will be described more specifically. The SAR management unit 215 performs control by the prediction and actual measurement of the SAR. The Q value $Q_{loaded}$ is used for the prediction of the SAR. This Q value $Q_{loaded}$ is obtained by being measured by the previous prescan of the present imaging sequence when the position of the subject 112 is determined. Further, in the prescan, reference power at which a 90-degree hydrogen spin falls is also measured in an imaging region where the subject is placed.

The SAR management unit 215 predicts an SAR from the reference power obtained in the prescan, at which the 90-degree hydrogen spin falls, the post-correction Q value $Q_{loaded}$ obtained in the Q-value calculation unit 213, and the waveform, strength and frequency of the RF signal in a subsequent imaging sequence. Specifically, the SAR management unit 215 calculates the subject consumed power $P_{object}$ being power given from each channel to the subject 112 by using the abovementioned formula (4) and determines a 10-second average of the sum of subject consumed power $P_{object}$ given by all channels, and a 6-minute average thereof as SARs. Then, it is discriminated whether the result of calculation conforms to a safety standard such as the IEC (International Electrotechnical Commission) or the like, for example, a standard such as 3 watts or less per weight 1 kg. When the result of calculation is unconformable, it is controlled to conform thereto.

More specifically, the whole body SAR is calculated by dividing $P_{object}$ by the weight of the subject.

That is, when the value of the SAR corresponding to the calculation result does not conform to the condition defined by the above safety standard, the SAR management unit 215 controls the SAR not to exceed a condition value stipulated in the standard by, for example, providing a pause period during the imaging, i.e., to conform to the safety standard. Alternatively, the SAR management unit 215 controls the SAR to conform to the safety standard by changing the waveform, strength and frequency of the irradiation RF signal.

The measuring instrument 202 continues the actual measurement of the RF signal applied to the subject even from the start of the present imaging. When the value actually measured by the measuring instrument 202 exceeds the predicted value by an estimated margin or more, the SAR management unit 215 determines that a problem occurs in safety, and issues a warning and urgently stops the apparatus.

The difference between the prediction and the actual measurement resides in that the value to be used as $P_{input}$ differs in the formula (4). In the prediction, $P_{input}$ is calculated and predicted from the reference power with the 90-degree fall and from the waveform, strength and frequency of the RF signal in its subsequent imaging sequence, whereas in the actual measurement, $P_{input}$ is actually measured.

The term of $Q_{loaded}$ in the formula (4) in the present embodiment takes the same value even in the prediction and the actual measurement. This value is determined by measurement during the prescan.

[Details of Q-Value Calculation Processing]

Subsequently, in the data processing unit 105 in the present embodiment, a description will be made about the details of Q-value calculation processing by the Q-value calculation unit 213 and the details of the SAR management by the SAR management unit 215 in particular.

(Forward Traveling Wave and Reflected Wave)

Figure 4:
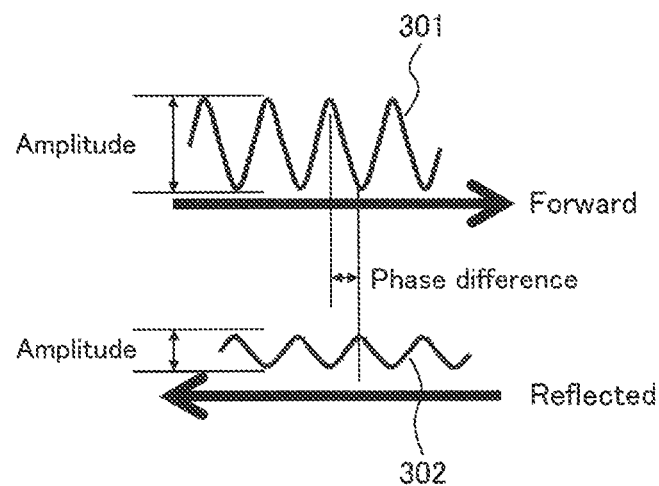
FIG. 4 is an explanatory diagram of a relation between the amplitudes and phases of forward traveling and reflected waves of an RF signal in the embodiment of the present invention.

First, a description will be made about the forward traveling wave and the reflected wave measured by the measuring instrument 202 of the data processing unit 105, which are required for calculation of the Q value. FIG. 4 is a diagram for describing an RF signal (RF wave) passing through a single transmission/reception cable (RF coaxial cable) 106. As described above, the RF wave passing through the transmission/reception cable 106 includes a forward traveling wave (input wave: Forward) 301 traveling from the amplifier 203 to the RF antenna 103, and a reflected wave (Reflected) 302 traveling from the RF antenna 103 to the amplifier 203, which is in a direction opposite to that of the forward traveling wave.

As shown in FIG. 4, the forward traveling wave 301 and the reflected wave 302 respectively have an amplitude (Amplitude) and a phase (Phase). Then, a phase difference is generated between the forward traveling wave 301 and the reflected wave 302.

Usually, a coaxial cable 106 of a 50-ohm (Ω) system is used for an RF signal ranging from a few MHz to a few 100 MHz applied to the MRI apparatus. When the input impedance (hereinafter simply referred to as "impedance") Z of the RF antenna 103 is properly matched to 50 ohms, the forward traveling wave 301 is hardly reflected. However, when the impedance Z of the RF antenna 103 is shifted from 50 ohms, the reflected wave 302 is generated.

The impedance Z of the RF antenna 103 greatly varies depending on the size, body composition and the like of the subject 112 disposed inside the RF antenna 103. When a large subject 112 is placed inside the RF antenna 103, and the subject 112 comes near the conductor of the RF antenna 103, the load of the RF antenna 103 becomes large, so that the impedance Z changes (decreases).

It is therefore difficult to adjust the impedance Z of the RF antenna 103 to 50 ohms in the state at imaging. Upon the actual imaging, the reflected wave 302 is generated in most cases.

A description will hereinafter be made of, as an example, a case where the number of channels to transmit the RF signal is four, and channel numbers of 1 to 4 are assigned in order. Absolute values $|S_{11}|$, $|S_{21}|$, $|S_{31}|$, and $|S_{41}|$ of the reflection coefficient S of the channel 1 are measured as follows. That is, an RF signal of a certain frequency $f_1$ is transmitted from the amplifier 203 to the channel 1. Assuming that the magnitude of power of the forward traveling wave at that time is $FWD_1(f_1)$, the magnitude of power of the reflected wave returned to the channel 1 of the amplifier 203 is $REF_{11}(f_1)$, and the magnitudes of power of the reflected waves returned to the channels 2, 3 and 4 of the amplifier 203 are respectively $REF_{21}(f_1)$, $REF_{31}(f_1)$ and $REF_{41}(f_1)$, the absolute value of the reflection coefficient S can be represented by the following formula (5):

$$|S_{n1}| = \sqrt{\frac{REF_{n1}(f1)}{FWD_1(f1)}} \quad (5)$$

where n=1~4

$|S_{11}|$ is measured by changing the frequency $f_1$ to about 10 to thereby determine a Q value of the channel 1 at the Q-value calculation unit 213. This Q value is a Q value calculated from only the diagonal terms of the reflection coefficient S of the RF antenna with coupling. Since the Q value is a value including the influence of the coupling, it is the abovementioned apparent Q value $Q_{appear}$.

Further, the absolute values of the non-diagonal terms $S_{21}$, $S_{31}$, and $S_{41}$ of the reflection coefficient S are obtained from the formula (5). Assuming that the frequency used for transmission of the MRI apparatus is $f_0$, $|S_{21}(f_0)|$, $|S_{31}(f_0)|$, and $|S_{41}(f_0)|$ are obtained. These values are used when correcting the Q value $Q_{appear}$ to calculate the original Q value.

Figure 5:
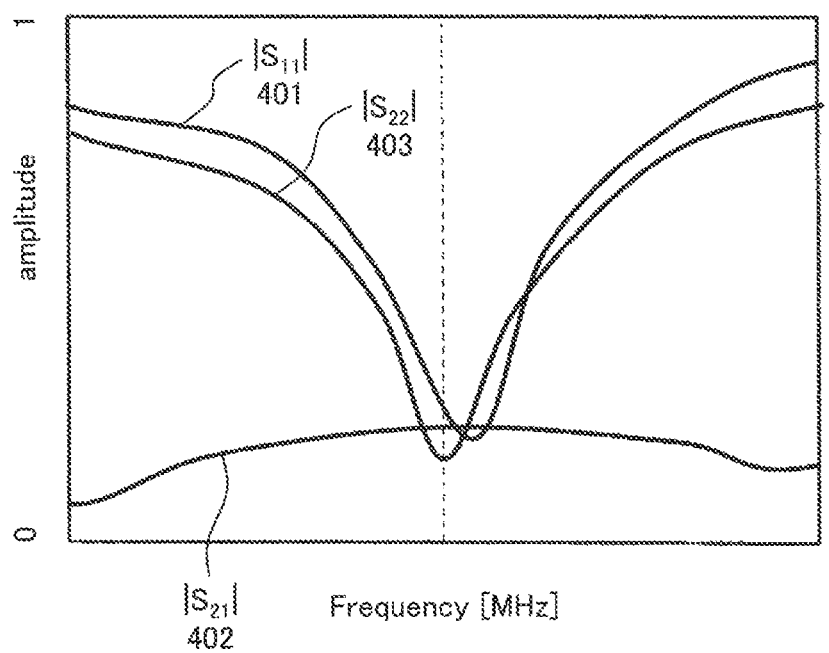
FIG. 5 is an explanatory diagram of an example in which diagonal and non-diagonal terms of measured reflection coefficients S in the embodiment of the present invention are graphed.

FIG. 5 is a graph of specific $|S_{11}|$, $|S_{22}|$, and $|S_{21}|$. In the graph shown in FIG. 5, the horizontal axis represents the frequency, and the vertical axis represents the reflection coefficient S or the coefficient of the reflection coefficient S. The diagonal terms of the reflection coefficient S become a curve in which the reflection coefficient S becomes close to zero at the resonant frequency and which is made convex downward in the graph of FIG. 5. On the other hand, the non-diagonal terms of the reflection coefficient S are values generally low at any frequency and often become a curve made concave upward in the graph of FIG. 5, in which the value thereof increases in the vicinity of the resonant frequency. The Q value is calculated using a frequency characteristic of the reflection coefficient S.

(Calculation of Apparent Q Value)

A description will subsequently be made about calculation processing of the apparent Q value, i.e., the Q value $Q_{appear}$ including the influence of the coupling.

In general, the Q value of the RF antenna 103 is calculated using the following formula (6):

[Formula 6]

$$Q = \frac{f(Z_{max})}{\delta f} \quad (6)$$

Where $f(Z_{max})$ is a frequency at which the absolute value $|Z_{11}|$ (hereinafter simply called impedance $|Z_{11}|$) of the impedance Z of the RF antenna 103 takes a peak value $(Z_{max})$. Also, $\delta f$ is a value of $1/\sqrt{2}$ of the peak value $(Z_{max})$ of the impedance $|Z_{11}|$, i.e., a difference between two frequencies at which a constant $y=Z_{max}/\sqrt{2}$ and a graph $y=|Z_{11}|$ intersect. That is, $\delta f$ is the width of the peak of the impedance $|Z_{11}|$.

The impedance Z of the RF antenna 103 is represented by the following formula (7-1) using the reflection coefficient S calculated from the forward traveling wave 301 and the reflected wave 302. Further, a formula (7-2) is an expression for converting the impedance Z to the reflection coefficient S.

[Formula 7]

$$Z = Z_0 \frac{1+S}{1-S} \quad (7-1)$$

$$S = \frac{Z-Z_0}{Z+Z_0} \quad (7-2)$$

Incidentally, $Z_0$ is the system characteristic impedance (usually 50 ohms).

Since the impedance Z is a complex value, the reflection coefficient S is also required to be obtained as a complex number. Therefore, the forward traveling wave 301 and the reflected wave 302 are also respectively required to be measured as a complex value. That is, when calculating the Q value by the above formula (6), it is usually necessary to measure not only the amplitudes of the forward traveling wave 301 and the reflected wave 302 but also their phases. Therefore, the values of L, C, and R are obtained by fitting from the impedance shown using a resonance circuit model shown in FIG. 7, the above formula (7-2), and the absolute value of each diagonal term of the reflection coefficient S.

That is, the Q-value calculation unit 213 in the present embodiment applies a plurality of different RF signals to the RF antenna 103 in the form of a load at the time of imaging, i.e., in a state in which the subject 112 is placed in the RF antenna 103 in the posture at the time of imaging, and measures the amplitudes of the power of the forward traveling wave 301 and the reflected wave 302 respectively. Then, the amplitude of the power of the reflected wave 302 is divided by the amplitude of the power of the forward traveling wave 301, and the absolute value $|S_{11}|$ of the diagonal term of the reflection coefficient S is calculated by taking the square root of its division result, whereby a function (S(f)) of a change in the reflection coefficient $|S_{11}|$ with respect to the frequency, which is represented in the graph (401, 402, 403) of FIG. 5 is determined.

Figure 7:
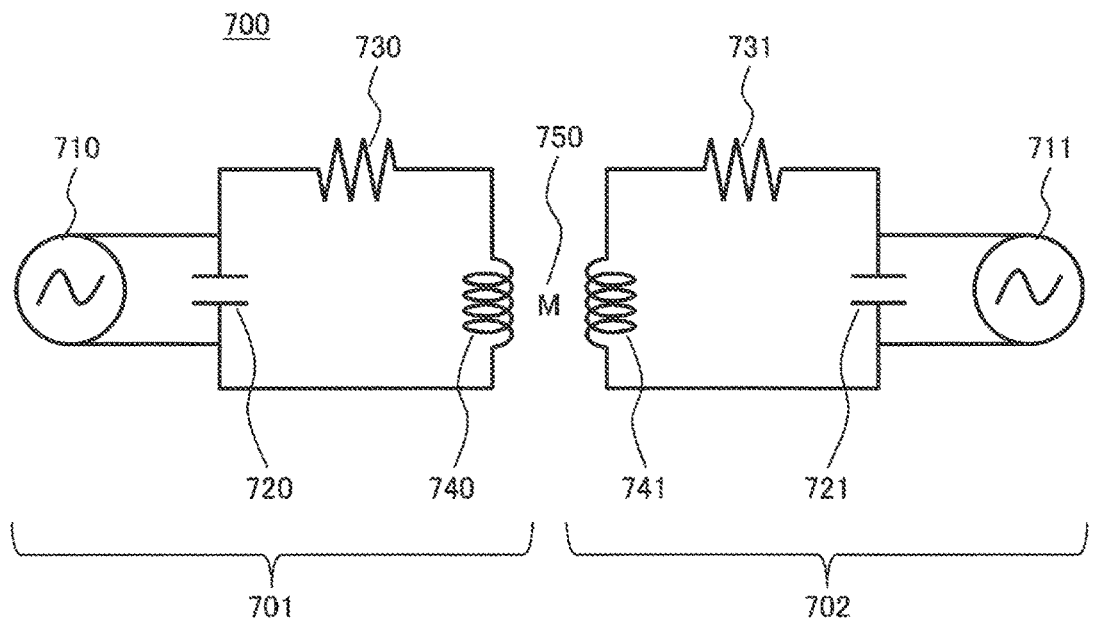
FIG. 7 is an explanatory diagram of a resonance circuit model in which an LCR resonance circuit is 2-channel simulated.

Each channel of the RF antenna 103 can be replaced with a simple LCR (inductor, capacitor and resistor) resonance circuit model in a narrow frequency range in the vicinity of its resonant frequency. A resonance circuit model 700 is shown in FIG. 7. The resonance circuit model 700 in FIG. 7 is equipped with two LCR resonance circuits 701 and 702. The LCR resonance circuit 701 is comprised of three circuit elements of an inductor 740, a capacitor 720, and a resistor 730 connected in series, which form a loop. Further, the LCR resonance circuit 702 is a parallel resonance circuit in which an RF frequency source 710 as a power feeding unit is connected in parallel with the capacitor 720. Likewise, the LCR resonance circuit 702 is also comprised of three circuit elements of an inductor 741, a capacitor 721, and a resistor 731.

Of the resonance circuit model 700, the LCR resonance circuit 701 can be represented by the following formula (8) using the inductance L of the inductor 740, the capacitance C of the capacitor 720, and the resistance value R of the resistor 730:

[Formula 8]

$$Z = \frac{\frac{1}{C\omega i}(L\omega i + R)}{\frac{1}{C\omega i} + L\omega i + R} \quad (8)$$

By substituting the formula (8) into the formula (7-2), the reflection coefficient S (reflection morphism coefficient) S of the 1-port LCR resonance circuit 701 is represented by L, C, R, and ω. Here, since ω is 2πf (f: frequency), the reflection coefficient S is represented by L, C, R, and the frequency f as expressed in the following formula (9). That is, it is a function of f.

[Formula 9]

$$S = \frac{2\pi f L i + R - Z_0(1 - LC \cdot (2\pi f)^2 + 2\pi f R C i)}{2\pi f L i + R + Z_0(1 - LC \cdot (2\pi f)^2 + 2\pi f R C i)} \quad (9)$$

Three different frequencies f are applied to the RF antenna 103, and the absolute value $|S_{11}|$ of each actually-measured reflection coefficient S is substituted into those obtained by taking the absolute values of both sides of the formula (9) to obtain three formulas. They are solved so that L, C, and R can also be determined. However, since such an exact solution is likely to give a solution far from reality for data large in measurement error, the Q-value calculation unit 213 of the present embodiment uses the least squares method easy to provide a limited range in solutions. Specifically, the frequency f is changed to three or more different values, which are respectively subjected to fitting by the least squares method assuming that each actually-measured reflection coefficient $|S_{11}|$ is taken as the absolute value of S in the above formula (9), and L, C, and R are taken as parameters, whereby effective values of L, C, and R are obtained.

The fitting makes use of, for example, an algorithm of a general-purpose non-linear least squares method fitting. That is, the values of L, C, and R are changed from their predetermined initial values by a predetermined amount of change in a predetermined range. Then, a set of values of L, C, and R where the square of the difference between the actually-measured value and the absolute value of the value obtained from the above formula (9) becomes the smallest is taken as solutions.

That is, the Q-value calculation unit 213 of the present embodiment performs fitting while changing the values of the respective circuit elements (inductor 740, capacitor 720, and resistor 730) to obtain the values (L, C, and R) of the respective circuit elements. Then, the Q value is calculated using the so-obtained values of the circuit elements (L, C, and R).

The Q value is calculated by the following formula (10):

[Formula 10]

$$\left. \begin{array}{l} ReZ_{max} = \dfrac{L}{CR} \\ \omega_0 = \dfrac{1}{\sqrt{LC}} \\ Q = \dfrac{L\omega_0}{R} = \dfrac{1}{R}\sqrt{\dfrac{L}{C}} \end{array} \right\} \quad (10)$$

Incidentally, $\omega_0$ is the resonance angular velocity of the LCR resonance system and becomes a resonance frequency $f_0$ divided by 2π.

That is, $\omega_0 = 2\pi f_0$. Accordingly, the real part $ReZ_{max}$ of the peak value $Z_{max}$ of the impedance of the RF antenna 103, the resonant frequency $f_0$ of the LCR resonance circuit 701, and the resonant Q value can also be similarly calculated by the formula (10) using these values of L, C, and R. Substituting $\omega_0$ of the formula (10) into the formula (8) determines $Z_{max} = L/(CR) + i\sqrt{L/C}$. Since, however, the imaginary part thereof is usually considerably smaller than the real part, $ReZ_{max}$ of the real part is taken as a typical parameter.

Thus, the apparent Q value is obtained by using the absolute value of each diagonal term of the reflection coefficient S.

(Calculation of Original Q Value)

The Q-value correction unit 213A obtains the original Q value obtained by removing the influence of the coupling, from the apparent Q value $Q_{appear}$ including the influence of the coupling.

Specifically, the original Q value is calculated by the following formula (11):

[Formula 11]

$$Q_{0_i} = Q_{appear_i} \left( 1 + \sum_{k=1,(k \neq i)}^{k=4} \frac{A \frac{\sum_{j=1}^{4} |S_{jj}^{2-n}|}{\sum_{m=1}^{4} |S_{mn}^{-n}|} + B}{\sqrt{Q_{appear_i} Q_{appear_k}}} \frac{|S_{ki}^2|}{1 - |S_{ii}^2|} \right) \quad (11)$$

Where A, B, and n are constants, in which n is a number greater than 0, and A and B are positive numbers. A, B, and n select such values that simulation is performed depending on various patient body shapes and how to enter the load, and the actual situation is reproduced in all cases. Further, i, j, k, and m are channel numbers of the high frequency antenna, $|S_{mm}|$, $|S_{jj}|$, and $|S_{ii}|$ are the absolute values of diagonal terms of the reflection matrix, and $|S_{kl}|$ indicates the absolute value of each non-diagonal term of the reflection matrix.

That is, the Q-value calculation unit 213 calculates the apparent Q value $Q_{appear}$ and n of each channel from the absolute value $|S_{nn}|$ (n: channel number) of the resulting diagonal term. After the completion of the acquisition of |S| and the apparent Q value $Q_{appear}$ in all channels, the Q-value correction unit 213A calculates, for each channel, the original Q value $Q_{0i}$ with the influence of the coupling removed therefrom in accordance with the above formula (11) by using the absolute value $|S_{kl}|$ of the non-diagonal term.

Incidentally, the description of deriving of the abovementioned formula (11) will be made later.

(Regarding Flow of Q-Value Calculation Processing and SAR Management)

Figure 6:
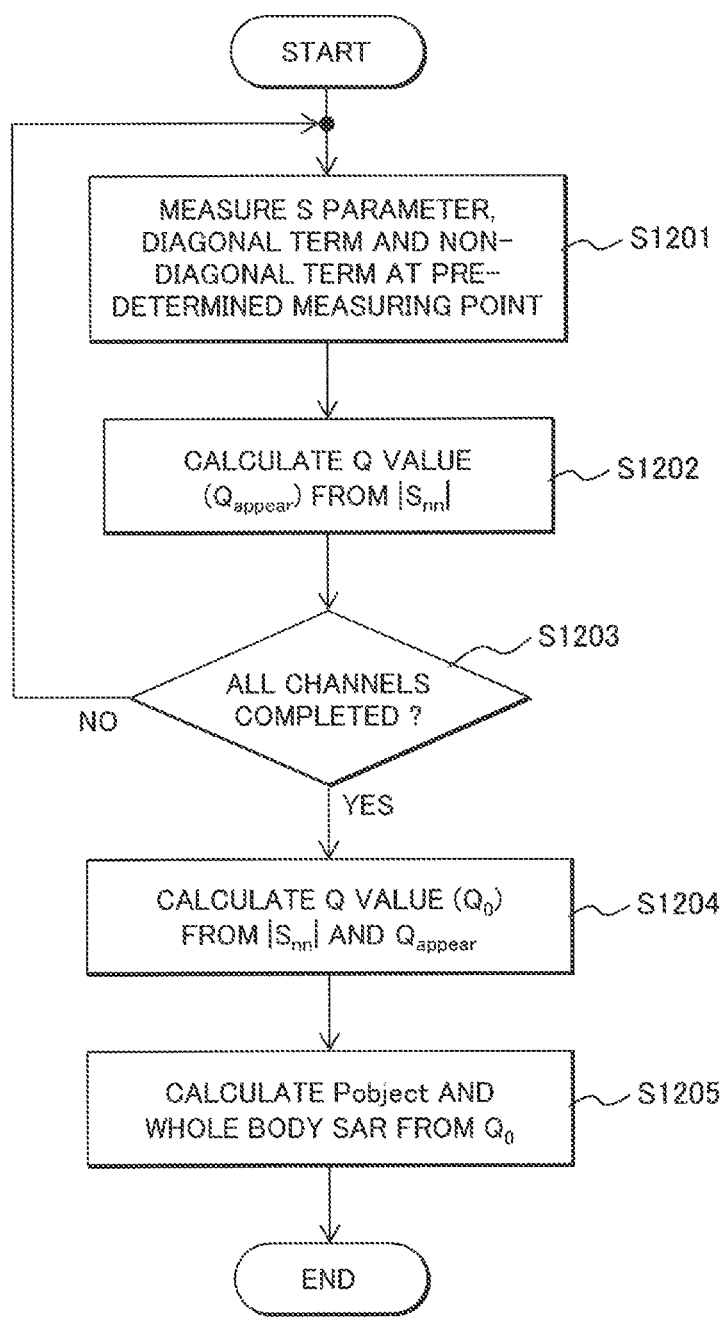
FIG. 6 is a flowchart showing a flow of processing up to Q-value calculation processing and an SAR calculation in the MRI apparatus according to the embodiment of the present invention.

Next, the flow of the original Q-value calculation processing and SAR management by the Q-value calculation unit 213 will be described in accordance with the flowchart of FIG. 6. At the time of imaging of the subject, the Q-value calculation unit 213 performs Q-value calculation processing in a state at its imaging, i.e., in a state of inserting the subject 112 each time the subject 112 is changed and each time the imaging region is changed. Further, the Q-value calculation processing is performed for each channel of the RF antenna 103.

The Q-value calculation unit 213 measures the amplitudes of the forward traveling and reflected waves 301 and 302 of each of RF signals having predetermined three or more different frequencies f, which are supplied to the high frequency antenna (RF antenna 103) and calculates each diagonal term $|S_{nn}|$ (where n indicates the channel number) and each non-diagonal term $|S_{nm}|$ (where n and m respectively indicate the channel number and n≠m) of the reflection coefficient S of each RF signal (Step S1201).

The RF signals having the predetermined three or more different frequencies f are supplied from the pulse generation unit 201 in accordance with an instruction from the supply unit 212. Then, the Q-value calculation unit 213 acquires the amplitudes of the forward traveling and reflected waves 301 and 302 at the time of supply of the RF signals of the respective frequencies f respectively and obtains the absolute value $|S_{nn}|$ of each diagonal term of the reflection coefficient and the absolute value $|S_{nm}|$ of each non-diagonal term thereof. The amplitudes of the forward traveling wave 301 and the reflected wave 302 are measured by the measuring instrument 202.

The Q-value calculation unit 213 acquires circuit constants (L, C, and R) by fitting the absolute value of each diagonal term of the reflection coefficient S to the predetermined resonance circuit model 700. Specifically, the values of the respective circuit elements L, C, and R in FIG. 7 are varied from their predetermined initial values in a predetermined manner to obtain functions S(f) with the frequency f as a variable, of the reflection coefficient S in the resonance circuit model 700, respectively. Then, for each function, the difference between the obtained respective reflection coefficients $|S_{11}|$ is calculated, and L, C, and R of the function in which the difference becomes the minimum are obtained as a solution.

Then, the Q-value calculation unit 213 calculates an apparent Q value $Q_{appear}$ of the high frequency antenna (RF antenna 103) by the formula (10) using the obtained circuit constants (Step S1202).

The Q-value calculation unit 213 performs the processing of Steps S1201 and S1203 for all channels (Step S1203) and proceeds to the next step S1204.

By repeating the above steps, Q-value acquisition is performed for not only the channel 1 but the remaining channels 2, 3, and 4, and the absolute value $|S_{nm}|$ of each non-diagonal term of the reflection coefficient S is used, whereby it is possible to perform the conversion to approximate the original Q value with the influence of the coupling removed therefrom from the apparent $Q_{appear}$ including the influence of the coupling. Specifically, the original Q value is calculated by the above formula (11) (Step S1204).

That is, the Q-value calculation unit 213 calculates the apparent Q value $Q_{appear}$ and n of each channel from the resulting $|S_{nn}|$ of each diagonal term. After the completion of acquisition of |S| and the apparent Q values $Q_{appear}$ in all channels, the Q-value correction unit 213A calculates, using their values, the original Q value $Q_0$ with the influence of the coupling removed therefrom for each channel in accordance with the above formula (11). Here, the calculated original Q value $Q_0$ is a Q value in a state in which the subject enters, and corresponds to $Q_{loaded}$ in the above formula (4).

Then, in Step S1205, as described above, the SAR management unit 215 takes the obtained original Q value $Q_0$ as $Q_{loaded}$, and takes as $Q_{empty}$, Q0 in a non-load state and with the influence of the coupling removed therefrom, which has been acquired in advance. And the SAR management unit 215 calculates $P_{object}$ from the above formula (4) using the known value of $P_{input}$ and calculates the SAR to perform SAR management.

(Derivation of Formula for Correcting Apparent Q Value at Q-Value Correction Unit)

Derivation of the above-described formula (11) will hereinafter be described using FIG. 7. Consider the resonance circuit model 700 in which as shown in FIG. 7, the two LCR resonance circuits 701 and 702 are coupled by a mutual inductance M750. The two LCR resonance circuits 701 and 702 respectively have the capacitors 720 and 721, the power feeding units 710 and 711 connected in parallel with the capacitors, the resistors 730 and 731, and the inductances 740 and 741. The circuit impedance of the resonance circuit model can be calculated by simulation using the known numerical computation software.

One impedance in one LCR resonance circuit of the resonance circuit model 700 shown in FIG. 7 can be written like the following formula (12) as seen from the power feeding unit:

[Formula 12]

$$Z = \frac{C\omega i^2 (L\omega i \| R)}{\frac{2}{C\omega i} + L\omega i + R} \quad (12)$$

Further, when considering the resonance circuit model shown in FIG. 7 as transmission circuits from left to right, their elements can be described by a method called an ABCD matrix. The part of the mutual inductance M in FIG. 7 can be represented like the following formula (13). Incidentally, the formula (13) is based on the non-patent literature 2.

[Formula 13]

$$\begin{bmatrix} A & B \\ C & D \end{bmatrix} = \frac{1}{k} \begin{bmatrix} \frac{1}{p} & \frac{j\omega M}{k} \\ \frac{k}{j\omega M} & p \end{bmatrix} \quad (13)$$

where $p = \sqrt{\frac{L_2}{L_2}}$, $k = \frac{M}{\sqrt{L_2 L_2}}$, $\sigma = 1 - k^2$

[Formula 14]

$$\begin{bmatrix} A & B \\ C & D \end{bmatrix} = \begin{bmatrix} 1 & 0 \\ C_1 \omega j & 1 \end{bmatrix} \begin{bmatrix} 1 & R_1 \\ 0 & 1 \end{bmatrix} \begin{bmatrix} \frac{L_1}{M} & j\omega\left(\frac{L_1^2}{M} - M\right) \\ \frac{1}{j\omega M} & \frac{L_1}{M} \end{bmatrix} \begin{bmatrix} 1 & R_2 \\ 0 & 1 \end{bmatrix} \begin{bmatrix} 1 & 0 \\ C_1 \omega j & 1 \end{bmatrix} \begin{bmatrix} 1 & 0 \\ \frac{1}{Z_0} & 1 \end{bmatrix} \quad (14)$$

Rewriting the LCR resonance circuits 701 and 702 of FIG. 7 in the ABCD matrix using the formula (13) can be represented like a formula (15).

However, in the formula (14), the impedance of a power supply of the power feeding unit 711 of the right LCR resonance circuit 702 in FIG. 7 is assumed to be $Z_0$ (normally 50Ω) and represents the ABCD matrix as seen from the power feeding unit 710 of the left LCR resonance circuit 701. Further, the capacitor, resistor and inductor of the LCR resonance circuit 701 are respectively expressed in $C_1$, $R_1$, and $L_1$, and the capacitor, resistor and inductor of the LCR resonance circuit 702 are respectively expressed in $C_2$, $R_2$, and $L_2$. Since A/C obtained by dividing the element A of the ABCD matrix by C indicates an impedance Z of a circuit represented by the ABCD matrix, the impedance of the resonance circuit model 700 coupled with M as seen from the power feeding unit 710 side can be determined by calculating the formula (14) to calculate A/C. If Z is determined by changing the value of M in various ways, and $Q_{appear}$ is determined from a graph having the peak of |Z|, $Q_{appear}$ when there is a coupling M is determined and can be compared with the following $Q_0$.

In the formula (13), $L_1$ is the capacitance of the inductor 740 in the LCR resonance circuit 701 of FIG. 7, and $L_2$ is the capacitance of the inductor 741 in the LCR resonance circuit 702 of FIG. 7.

Further, the original Q values of the two LCR resonance circuits 701 and 702 in FIG. 7 can be defined by the following formula (15):

[Formula 15]

$$Q_0 = \frac{1}{R}\sqrt{\frac{L}{C}} \quad (15)$$

When $M/L_1$ is increased from 0.0005 to 0.005 where the resonance circuit model 700 shown in FIG. 7 is created near 123 MHz being the resonant frequency of the 3-tesla MRI apparatus, and the original Q value of the LCR resonance circuit 701 of the resonance circuit model 700 is assumed to be 317, an impedance graph as seen from the power feeding unit 710 of the LCR resonance circuit 701 is made to thereby enable the apparent $Q_{appear}$ to be read. When the two LCR resonance circuits 701 and 702 are coupled while increasing the value of the mutual inductance M, the apparent $Q_{appear}$ is reduced from 317 of the original $Q_0$. When the $M/L_1$ is increased to 0.005, the apparent $Q_{appear}$ is reduced to 0.45 times the original Q value. It is shown in FIG. 8 that this relation is plotted.

Figure 8:
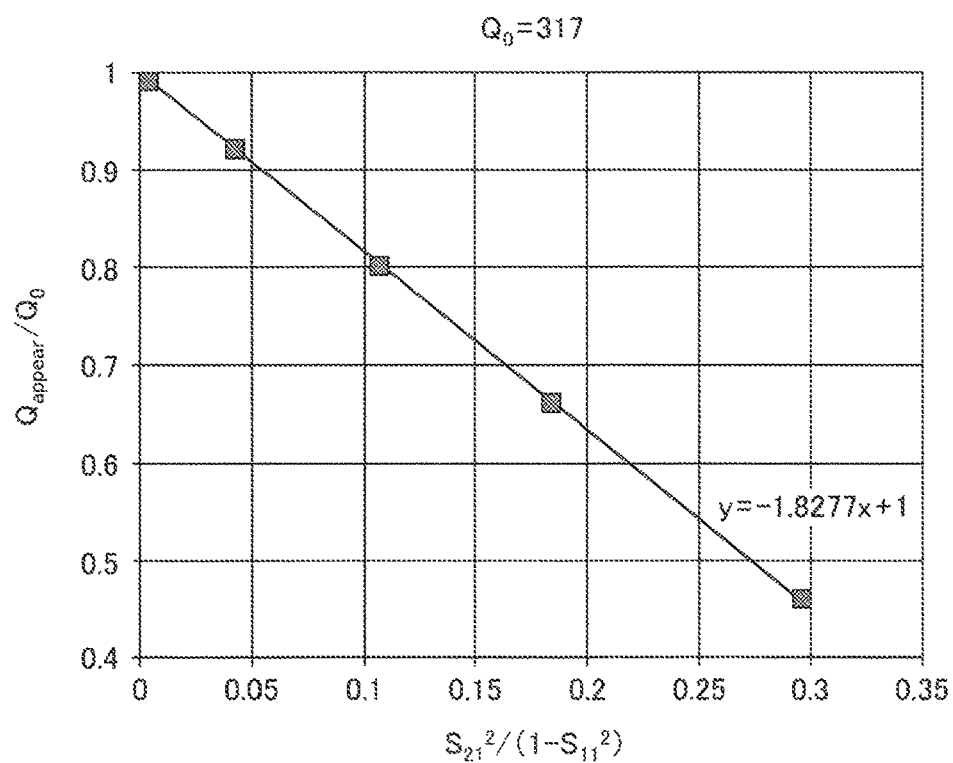
FIG. 8 is an impedance graph as viewed from a power feeding unit 710 where the original Q-value of an LCR resonance circuit 701 is assumed to be 317 in the LCR resonance circuit of FIG. 7.

In FIG. 8, those calculated as $S_{21}^2/(1-S_{11}^2)$ using a non-diagonal term $S_{21}$ and a diagonal term $S_{11}$ of the reflection coefficient S are plotted in the horizontal axis. The fallen condition of the apparent Q, $Q_{appear}/Q_0$ is plotted in the vertical axis. Since these plots are located on a substantially straight line, a formula (16) is established with a as a constant.

[Formula 16]

$$\frac{Q_{appear}}{Q_0} = 1 - \frac{a + S_{22}^s}{1 - S_{ss}^2} \quad (16)$$

The value of the constant a has been found to be related to the original Q value $Q_0$. More specifically, the relation between the constant a and the original Q value $Q_0$ such as a case in which the value of the constant a is roughly proportional to $1/\sqrt{(Q_{01} * Q_{02})}$ assuming that the original Q value of the left circuit in FIG. 7 is $Q_{01}$, and the original Q value of the right circuit is $Q_{02}$ is found by circuit simulation.

Then, when the formula (16) is extended to four channels, it can be represented like a formula (17).

[Formula 17]

$$\frac{1}{Q_{0i}} = \frac{1}{Q_{appear,i}}\left(1 - \sum_{j=1,(j\neq i)}^{4} \frac{a}{\sqrt{Q_{0i}Q_{0j}}} \frac{S_{ji}^2}{1-S_{ii}^2}\right) \quad (17)$$

In the formula (17), $Q_{0i}$ is the original Q value of the channel i, $Q_{appear,i}$ is the apparent Q value of the channel i, and the coefficient a is a constant. Since it is preferably possible to solve the formula (12) for $Q_{0i}$, but the formula (16) itself is complex and cannot be deformed simply, this is made approximate. Assuming that in the formula (17), the right-side $Q_{0i}$ and $Q_{0j}$ are respectively approximated by $Q_{appear,i}$ and $Q_{appear,j}$ and the terms subsequent to the square of the Taylor expansion of $1/(1-x)=1+x+x^2$ are ignored, the formula (17) can be approximated like a formula (18):

[Formula 18]

$$Q_{0i} = Q_{appear,i}\left(1 + \sum_{j=1,(j\neq i)}^{4} \frac{a}{\sqrt{Q_{appear,i}Q_{appear,j}}} \frac{S_{ji}^2}{1-S_{ii}^2}\right) \quad (18)$$

The value of the constant a and $S_{11}$, $S_{22}$, $S_{33}$, and $S_{44}$ were found to be correlated therebetween as a result of the fact that various human body models from a child having a body weight of 18 kg to a fat human having a body weight of 120 kg were arranged in various imaging sites from head to ankle and subjected to simulation using the formula (18). Among the values from $S_{11}$ to $S_{44}$, the value of |S| of the channel in which reflection is small, i.e., the value of |S| is close to zero, and a are correlated. That is, assuming that the channel small in reflection is 2 and 3, the original Q value $Q_{0i}$ can be represented like a formula (19). Coefficients b and c are position constants.

[Formula 19]

$$Q_{0i} = Q_{appear,i}\left(1 + \sum_{j=1,(j\neq i)}^{4} \frac{c(S_{22}^2 + S_{33}^2) + b}{\sqrt{Q_{appear,i}Q_{appear,j}}} \frac{S_{ji}^2}{1-S_{ii}^2}\right) \quad (19)$$

It was found that overestimation of the SAR could be almost solved by converting the apparent Q value $Q_{appear}$ to the original $Q_0$ using the above-described formula (19) and calculating $P_{object}$ using the formula (4). In the above-described formula (19), there occurs 4-channel nonequivalent work of choosing two channels low in the value of |S|. Therefore, as a function to increase the weight where the value of |S| is low, a formula (20) is applied to the part of $S_{22}^2 + S_{33}^2$. Incidentally, n is a number greater than 0 in the formula (20).

[Formula 20]

$$\frac{\sum_{j=1}^{4}(|S_{jj}^{-n}||S_{jj}^2|)}{\sum_{m=1}^{4}|S_{mm}^{-n}|} = \frac{\sum_{j=1}^{4}|S_{jj}^{2-n}|}{\sum_{m=1}^{4}|S_{mm}^{-n}|} \quad (20)$$

Thus, it is possible to finally obtain the formula (11) of correcting the apparent Q value to calculate the original Q value.

As described above, the MRI apparatus 100 according to the present embodiment is equipped with the high frequency antenna 103 which resonates at the predetermined frequency, the supply unit 212 which supplies each high frequency signal to the high frequency antenna 103, the measuring instrument 202 which measures the amplitudes of the forward traveling wave 301 and the reflected wave 302 of the high frequency signal supplied from the supply unit 212 to the high frequency antenna 103, and the Q-value calculation unit 213 which calculates the Q values of the plural channels of the high frequency antenna 103 using the amplitudes respectively. The supply unit 212 supplies each high frequency signal to the high frequency antenna 103. The measuring instrument 202 measures the amplitudes with respect to the supplied high frequency signal of each frequency respectively. The Q-value calculation unit 213 calculates the apparent Q value from each diagonal term having the absolute value of the reflection coefficient obtained from the amplitudes. Further, after the Q values in all channels and the diagonal and non-diagonal terms having the absolute values of the reflection coefficient are obtained, the apparent Q value is corrected to calculate the original Q value.

A table 1 shows results obtained by performing electromagnetic field numerical simulation on the 4-channel irradiation coils and the various loads placed thereinside. A simulation was performed for as the human body models, five types of FATS (body weight 115 kg required to be confirmed), Hugo (body weight 90 kg), Roberta (18 kg), Child (8 kg), and Hanako (50 kg), and for as the imaging regions, six types of head (head part), Abd (abdominal part), LSP (lumbar part), Knee (knee region), Ankle (ankle region), and Breast (breast region). Further, even as for the aqueous solution prepared by dissolving salt called phantom, a simulation was performed for four types of Bottle11 (30 kg), Bottle13 (3 kg), Bottle14 (2 kg), and case1 (30 kg) inclusive of two cases where they were arranged in the center and arranged on the CH1 and CH2 sides.

Incidentally, the above-described human body models FATS, Roberta, and Child are those bought from The Foundation for Research on Information Technologies in Society (IT'IS) in Switzerland. Hugo is one developed by Visible Human Project (trademark registered) of National Library of Medicine of US NIH. Further, Hanako is a human body model database developed jointly by National Institute of Information and Communication Technology, Kitasato University, Keio University, and Tokyo Metropolitan University in Japan.

Table 1: List (row) of simulation used for evaluation (row) and results of SAR excessive evaluation (column)

TABLE 1

| | | | SAR excessive degree | |
| --- | --- | --- | --- | --- |
| Model | Position | P/P (Smn) | Conventional method | Present embodiment |
| FATS | Head | 0.902 | 1.556 | 1.232 |
| Hugo | Head | 0.805 | 1.715 | 1.326 |
| Roberta | Head | 0.611 | 1.646 | 1.319 |
| Bottle11 | Center | 1.133 | 1.760 | 1.223 |
| case1 | Center | 1.116 | 1.675 | 1.101 |
| Hugo | Abd | 1.784 | 1.181 | 1.070 |
| Roberta | LSP | 1.246 | 1.205 | 1.016 |
| FATS | LSP | 2.066 | 1.169 | 1.109 |
| Roberta | Knee | 0.885 | 1.271 | 1.113 |

TABLE 1-continued

| | | | SAR excessive degree | |
| Model | Position | P/P (Smn) | Conventional method | Present embodiment |
| --- | --- | --- | --- | --- |
| FATS | Knee | 1.428 | 1.291 | 1.126 |
| Hugo | Knee | 1.438 | 1.341 | 1.186 |
| Hugo | LSP | 1.767 | 1.283 | 1.129 |
| Roberta | Head | 0.667 | 1.506 | 1.221 |
| Child_8 kg | Head | 0.471 | 1.614 | 1.126 |
| Roberta | LSP | 1.292 | 1.162 | 1.004 |
| Hanako | LSP | 1.452 | 1.204 | 1.046 |
| Bottle11 | Center | 1.179 | 1.624 | 1.163 |
| bottle13 | Center | 0.245 | 1.359 | 0.958 |
| Hanako | Ankle | 0.655 | 1.340 | 1.236 |
| bottle14 | Center | 0.062 | 1.702 | 1.126 |
| bottle11 | CH12side | 1.644 | 1.103 | 0.945 |
| Fats | Breast | 2.085 | 1.142 | 1.005 |
| | | | Average 1.402 | 1.126 |
| | | | Std. 0.221 | 0.106 |

In the electromagnetic field numerical simulation, the reflection coefficient (reflection matrix) S of the antenna, the incident power ($P_{input}$) and energy consumption ($P_{object}$) by the human body or phantom are obtained. $Q_{appear}$, $|S_{nm}|$, and $|S_{nm}|$ are calculated from the obtained reflection coefficient S, and $Q_0$ which is the original Q value is calculated.

$P_{object}$ (this is $P_{object\_fromS}$) calculated using the original Q value as the Q value of the formula (4), and $P_{object}$ (this is $P_{object\_fromField}$) directly calculated from an electromagnetic field distribution by simulation are compared. The ratio of $P_{object\_fromS}/P_{object\_fromField}$ is described as a SAR excessive degree in the above Table 1 and the following Table 2.

Incidentally, Table 2 shows a result obtained by appropriately substituting a value into A, B, and n. It was found that when n=1, Average was close to 1, and the distribution was small.

TABLE 2

| | Average of All examples of SAR excessive ratio | Standard deviation of all examples of SAR excessive ratio | A | B |
| --- | --- | --- | --- | --- |
| Calculation at $Q_{appear}$ (conventional method) | 1.402 | 0.221 | — | — |
| n = 0.5 | 1.155 | 0.118 | 1500 | 200 |
| n = 1 | 1.139 | 0.110 | 900 | 240 |
| n = 1 | 1.126 | 0.106 | 1200 | 250 |
| n = 2 | 1.132 | 0.107 | 1000 | 260 |
| n = 3 | 1.132 | 0.110 | 1100 | 270 |
| n = 8 | 1.155 | 0.124 | 1200 | 270 |

Table 2 has shown results calculated by giving various numbers to mainly n of the parameters A, B, and n shown in the formula (11). The "conventional method in Tables 1 and 2 is a calculation result obtained by calculating the subject consumed power $P_{object}$ from the formula (4) using the apparent Q value $Q_{appear}$ while leaving the influence of the coupling.

Results obtained by comparing, in detail for each simulation condition, the case of n=1, A=1200 and B=250 with the conventional case in Table 2 were shown in the right two columns of Table 1.

As shown in Table 2, assuming that n=1, A=1200, and B=250 in the formula (11), the apparent Q value $Q_{appear}$ is corrected to calculate the original Q value $Q_0$. The SAR value calculated using it is reduced to 1.126 times in SAR excessive degree although the SAR excessive degree has conventionally been 1.402 times.

For reference, it was found from a calculation by similar simulation that as a result of a trial calculation by the method in Patent Literature 1, the excessive degree of SAR was only reduced to about 1.26 times.

It is understood that when the right two columns in Table 1 are compared, the excessive estimation degree of SAR is high where the relatively small subject such as the head, the phantom or the like is placed inside the irradiation coils, and the calculation result in the present embodiment is reduced more than the calculation result by the conventional method. On the other hand, it is understood that even when viewing the result of the human body model other than the phantom in the present embodiment, there is no calculation example in which the SAR excessive estimation degree falls below 1, and the risk for the patient is not increased either by estimating the SAR too small.

Thus, according to the present embodiment, even when the RF antenna has the plural channels, it is possible to calculate the Q value by using the values measurable by the existing hardware of the MRI apparatus and correct the same to thereby calculate the accurate Q value. That is, at the time of the imaging, after the subject is arranged, the apparent Q value including the influence of coupling that occurs between the plural channels is calculated from the value obtained by the transmission of each RF signal. This is measured inclusive of each non-diagonal term of the reflection coefficient for each channel. The apparent Q value can be converted into the original Q value by correcting the same. Accordingly, the accurate Q value can be obtained by only the existing hardware without mounting a new expensive measuring instrument and without significantly extending the imaging time from the normal imaging time. That is, according to the present embodiment, it is possible to perform SAR management more highly accurately by avoiding overestimation of the SAR calculation value without increasing the apparatus cost and without extending the processing time.

Since the SAR management in the conventional MRI imaging is affected by the coupling between the channels, the SAR is apt to be excessively estimated where the SAR is simply estimated from only each diagonal term of the reflection coefficient matrix S, thus resulting in disadvantages such as the imaging time being extended, the image quality being degraded, and the number of photographed images being reduced. Further, in order to estimate accurately, there is a need to measure the Q values in all channels of the RF antenna 103 for each patient imaging region, i.e., to measure the amplitudes and phases of the forward traveling and reflected waves. However, an expensive measuring instrument is required for the measurement of the Q value, and time is also required therefor.

According to the present embodiment, such problems with the prior art can be solved, and the Q value can be obtained with satisfactory accuracy without adding new hardware to the MRI apparatus 100 and without also increasing the burden of a patient. Accurate SAR management is made possible using the highly accurate Q value.

Incidentally, although it has been described in the above-described embodiment that the Q value is calculated in the MRI apparatus to perform the SAR management, the present embodiment can be applied not only to the MRI apparatus, but also any apparatus which needs to use an electromagnetic wave having a frequency from a few kHz to a few GHz and manage the transmission power of the electromagnetic wave and the SAR at which the transmission power is applied to the human body.

Further, the data processing unit 105 in the present embodiment is equipped with a CPU, a memory, and a storage device. Then, each function realized by the data processing unit 105 is implemented by causing the CPU of the data processing unit 105 to load a program stored in the storage device into the memory and to execute the same. Also, all or some of the functions may be realized by hardware such as an ASIC (Application Specific Integrated Circuit), an FPGA (field-programmable gate array), or the like. Further, various data used for processing of each function, and various data generated during the processing are stored in the storage device.

Incidentally, the embodiments of the present invention are not limited to the above-described embodiments. Various additions and changes, etc. can be made within the scope not departing from the spirit of the invention.

REFERENCE SIGNS LIST

100: MRI apparatus, 101: magnet, 102: gradient magnetic field coil, 103: RF antenna, 104: transceiver, 105: data processing unit, 106: transmission/reception cable, 107: gradient magnetic field control cable, 108: display device, 109: gradient magnetic field power source, 111: bed, 112: subject, 201: pulse generation unit, 202: measuring instrument, 203: amplifier, 212: supply unit, 213: Q-value calculation unit, 213: Q-value correction unit, 214: reflection coefficient determination unit, 215: SAR management unit, 216: power calculation unit, 301: forward traveling wave, 302: reflected wave, 700: resonance circuit model, 701: LCR resonance circuit, 702: LCR resonance circuit, 710: RF frequency source, 720: capacitor, 730: resistor, 740: inductor, 750: mutual inductance coefficient M.

The invention claimed is:

1. A magnetic resonance imaging apparatus comprising:
a high frequency antenna which has a plurality of channels and resonates at a predetermined frequency;
a supply unit which supplies a plurality of high frequency signals having different frequencies to the high frequency antenna;
a measuring instrument which measures the amplitudes of a forward traveling wave and a reflected wave of each of the high frequency signals supplied from the supply unit to the high frequency antenna;
a Q-value calculation unit which calculates a Q value for each of the channels by fitting an absolute value of each diagonal term of a reflection matrix S calculated based on the amplitudes measured by the measuring instrument to a predetermined circuit model; and
a Q-value correction unit which corrects the Q value calculated by the Q-value calculation unit using an absolute value of each non-diagonal term of the reflection matrix S.

2. The magnetic resonance imaging apparatus according to claim 1, wherein the Q-value correction unit estimates the ratios of energy consumed by the high frequency antenna, of energy of the high frequency signals input to the high frequency antenna, and energy thereof consumed in a subject disposed near the high frequency antenna to thereby correct the Q value.

3. The magnetic resonance imaging apparatus according to claim 1, wherein the Q-value correction unit corrects the Q value $Q_{appear}$ calculated by the Q-value calculation unit in accordance with the following formula to thereby acquire a Q value $Q_{0i}$:

$$Q_{0i} = Q_{appear_i} \left\{ 1 + \sum_{k=1,(k \neq i)}^{k=M} \frac{A \frac{\sum_{j=1}^{M} |S_{jj}^{2-n}|}{\sum_{m=1}^{M} |S_{mm}^{-n}|} + B}{\sqrt{Q_{appear_i} Q_{appear_k}}} \frac{|S_{ki}^2|}{1 - |S_{ii}^2|} \right\}$$

where A, B, and n are constants determined according to the subject, in which n is a number greater than 0, and A and B are positive numbers. Further, i, j, k, and m represent channel numbers of the high frequency antenna, M represents a channel number, $|S_{mm}|$, $|S_{jj}|$, and $|S_{ii}|$ represent the absolute values of the diagonal terms of the reflection matrix, and $|S_{ki}|$ represents the absolute value of the non-diagonal term of the reflection matrix.

4. The magnetic resonance imaging apparatus according to claim 1, further comprising a specific absorption rate management unit which calculates, using the Q-value corrected by the Q-value correction unit, irradiation power consumed in the subject among irradiation power by the high frequency signals supplied to the high frequency antenna at the time of imaging to manage a specific absorption rate.

5. A Q-value calculating method comprising:
a reflection coefficient calculation step of measuring the amplitudes of a forward traveling wave and a reflected wave of each high frequency signal supplied to a high frequency antenna having a plurality of channels to calculate the absolute values of diagonal and non-diagonal terms of a reflection matrix of the high frequency signals for each of the channels;
a Q-value calculation step of fitting the absolute value of each diagonal term of the reflection matrix to a predetermined circuit model to thereby calculate a Q value for each of the channels; and
a correction step of correcting the Q value calculated by the Q-value calculation step using the absolute value of each non-diagonal term of the reflection matrix.

6. A specific absorption rate managing method comprising:
a reflection coefficient calculation step of measuring the amplitudes of a forward traveling wave and a reflected wave of each high frequency signal supplied to a high frequency antenna having a plurality of channels to calculate the absolute values of diagonal and non-diagonal terms of a reflection matrix of the high frequency signals for each of the channels;
a Q-value calculation step of fitting the absolute value of each diagonal term of the reflection matrix to a predetermined circuit model to thereby calculate a Q value for each of the channels;
a correction step of correcting the Q value calculated by the Q-value calculation step using the absolute value of each non-diagonal term of the reflection matrix; and
a specific absorption rate management step of calculating, using the corrected Q value, irradiation power consumed in a subject among irradiation power by the high frequency signals supplied to the high frequency antenna to manage a specific absorption rate.

* * * * *